United States Patent [19]

Messmer et al.

[11] Patent Number: 4,602,018
[45] Date of Patent: Jul. 22, 1986

[54] CONDENSED AS-TRIAZINE DERIVATIVES

[75] Inventors: András Messmer; Sándor Bátori; György Hajós; Pál Benkó, all of Budapest, Hungary

[73] Assignee: Egyt Gyogyszevegyeszeti Gyar, Budapest, Hungary

[21] Appl. No.: 652,612

[22] Filed: Sep. 20, 1984

[30] Foreign Application Priority Data

Sep. 20, 1983 [HU] Hungary .............................. 3242/83

[51] Int. Cl.⁴ .................... C07D 253/08; A61K 31/53
[52] U.S. Cl. ...................................... 514/243; 544/183
[58] Field of Search ........................ 544/183; 514/243

[56] References Cited

U.S. PATENT DOCUMENTS 4,419,355  12/1983  Kosoczky et al. .................. 544/183

FOREIGN PATENT DOCUMENTS 2081261  2/1982  United Kingdom ................ 544/183

*Primary Examiner*—John M. Ford
*Attorney, Agent, or Firm*—Keil & Weinkauf

[57] ABSTRACT

The invention relates to new condensed as-triazine derivatives of the general Formula I

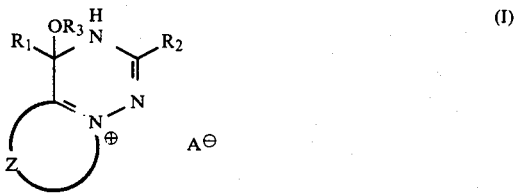

and isomers thereof (wherein
$R_1$ stands for $C_{1-10}$ alkyl or phenyl or naphthyl, wherein the two latter groups may be optionally substituted by one or more halogen, nitro, amino, hydroxy, $C_{1-4}$ alkyl and/or $C_{1-4}$ alkoxy substituent(s);
$R_2$ is hydrogen, $C_{1-4}$ alkyl, hydroxy, halogen or phenyl or naphthyl, wherein the two latter groups may be optionally substituted by one or more halogen, nitro, amino, hydroxy, $C_{1-4}$ alkyl and/or $C_{1-4}$ alkoxy substituent(s);
$R_3$ represents hydrogen or $C_{1-4}$ alkyl;
Z is buta-1,3-dienyl or a group of the Formula (a)

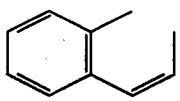

or (b)

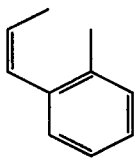

and
$A^-$ is an anion).

The compounds of the general Formula I possess useful pharmacological properties, particularly antiarrhythmial and antidepressant effect.

8 Claims, No Drawings

CONDENSED AS-TRIAZINE DERIVATIVES

This invention relates to pharmaceutically active new condensed as-triazine derivatives, a process for the preparation thereof and pharmaceutical compositions containing the same.

According to an aspect of the present invention there are provided new condensed as-triazine derivatives of the general Formula I

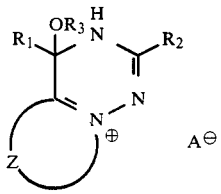

(I)

and isomers thereof, wherein
$R_1$ stands for $C_{1-10}$ alkyl or phenyl or naphthyl, wherein the two latter groups may be optionally substituted by one or more halogen, nitro, amino, hydroxy, $C_{1-4}$ alkyl and/or $C_{1-4}$ alkoxy substituent(s);
$R_2$ is hydrogen, $C_{1-4}$ alkyl, hydroxy, halogen or phenyl or naphthyl, wherein the two latter groups may be optionally substituted by one or more halogen, nitro, amino, hydroxy, $C_{1-4}$ alkyl and/or $C_{1-4}$ alkoxy substituent(s);
$R_3$ represents hydrogen or $C_{1-4}$ alkyl;
Z is buta-1,3-dienyl or a group of the Formula (a)

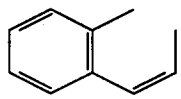

(a)

or (b)

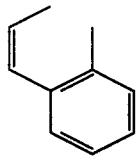

(b)

and
$A^-$ is an anion.

The term "alkyl" used throughout the specification relates to straight or branched chain alkyl groups (e.g. methyl, ethyl, n-propyl, isopropyl, tertiary butyl etc.). The term "alkoxy" relates to straight or branched chained alkoxy groups (e.g. methoxy, ethoxy, isopropoxy etc.). The term "halogen" encompasses the fluorine, chlorine, bromine and iodine atoms.

According to a preferred feature of the present invention there are provided compounds of the general Formula I, wherein Z is a group of the Formula (b). $R_1$ represents preferably a phenyl group optionally substituted by one or more halogen atom(s), particularly 4-chloro-phenyl.

$R_2$ stands preferably for hydrogen and $R_3$ is preferably hydrogen.

Particularly preferred representatives of the compounds of the general Formula I are the following derivatives:

1-(4-chloro-phenyl)-1-hydroxy-1,2-dihydro-as-triazino-[6,1-a]isoquinolinium-ethanesulfonate;
1-(4-chloro-phenyl)-1-hydroxy-1,2-dihydro-as-triazino-[6,1-a]isoquinolinium-chloride.

$A^-$ may stand for any pharmaceutically acceptable inorganic or organic anion (e.g. chloride, bromide, iodide, perchlorate, methane sulfonate, ethane sulfonate etc.).

According to a further aspect of the present invention there is provided a process for the preparation of compounds of the general Formula I and isomers thereof, which comprises ($a_1$) for the preparation of compounds of the general Formula I, wherein $R_3$ is hydrogen, reacting a compound of the general Formula II

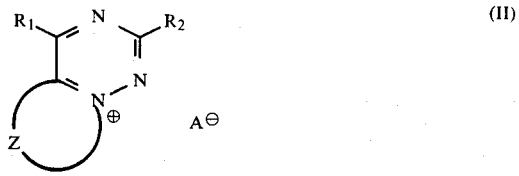

(II)

wherein $R_1$, $R_2$, Z and $A^-$ are as stated above, with water; or ($a_2$) for the preparation of compounds of the general Formula I, wherein $R_3$ is hydrogen, reacting a compound of the Formula IV

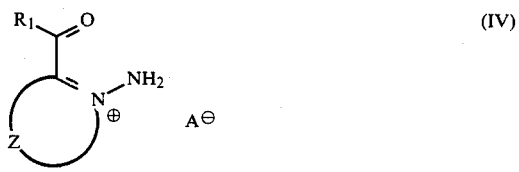

(IV)

wherein $R_1$, Z and $A^-$ are as stated above, with a compound of the general Formula V $$NH_2-CO-R_4 \qquad (V)$$

wherein $R_4$ is hydrogen, $C_{1-4}$ alkyl or optionally substituted phenyl, in the presence of a dehydrating agent and treating the reaction mixture with water; or (b) reacting a compound of the general Formula III

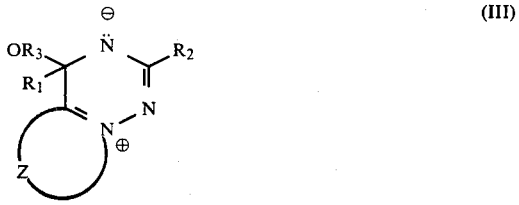

(III)

(wherein $R_1$, $R_2$, $R_3$ and Z are as stated above) with an acid of the general Formula VIII $$H-A \qquad (VIII)$$

(wherein $A^-$ is as stated above); or (c) for the preparation of compounds of the general Formula I, wherein $R_3$ is hydrogen and $R_2$ stands for hydrogen, $C_{1-4}$ alkyl or unsubstituted phenyl, reacting a compound of the general Formula IV (wherein $R_1$, Z and $A^-$ are as stated above) with an ortho-ester of the general Formula VI $$R_6C/OR_5/_3 \quad (VI)$$

(wherein $R_5$ is $C_{1-4}$ alkyl and $R_6$ stands for hydrogen, $C_{1-4}$ alkyl or unsubstituted phenyl) and subjecting the formimino-ether of the general Formula VII

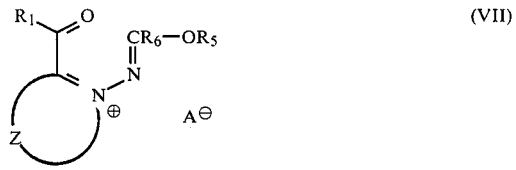

thus obtained (wherein $R_1$, $R_5$, $R_6$, Z and $A^-$ are as stated above) to ring closure by reacting with ammonia; or (d) for the preparation of compounds of the general Formula I, wherein $R_3$ is $C_{1-4}$ alkyl, reacting a compound of the general Formula II with a metal alcoholate containing 1-4 carbon atoms; or (e) for the preparation of compounds of the Formula I, wherein $R_3$ is hydrogen and $R_2$ stands for halogen, reacting a compound of the Formula IV with urea in the presence of an organic solvent and a halogen-containing dehydrating agent, and, if desired, separating a compound of the Formula I thus obtained into the isomers thereof and/or exchanging an $A^-$ anion for an other $A^-$ anion.

According to method $a_1$, compounds of the Formula I, wherein $R_3$ is hydrogen, are prepared by reacting a compound of the Formula II with water. The reaction may be carried out in any suitable water-miscible organic solvent or water or a mixture of a water-miscible organic solvent and water. As water-miscible organic solvent e.g. alkanols (e.g. methanol, ethanol), aliphatic or cyclic ethers (e.g. diethyl ether, dioxane or tetrahydrofurane), esters (e.g. ethyl acetate) or acetonitrile may be used. It is preferred to use a mixture of water and acetonitrile as reaction medium. The reaction may be accomplished at a temperature between 5 C.° and 50 C.°, preferably at room temperature.

According to method $a_2$, compounds of the Formula I, wherein $R_3$ is hydrogen, are prepared by reacting a compound of the general Formula IV with a compound of the Formula V and treating the reaction mixture with water. The reaction of the compounds of the Formulae IV and V is carried out in the presence of a dehydrating agent. For this purpose preferably a Lewis acid—e.g. titanium tetrachloride, aluminium chloride or boron trifluoride etc.—or phosphorous oxychloride may be used. The reaction may be accomplished at a temperature between 50 C.° and 120 C.°, particularly at 80-90 C.°. As reaction medium inert organic solvents may be used, e.g. halogenated hydrocarbons (e.g. chloroform, chlorobenzene etc.), aromatic hydrocarbons (e.g. xylene, toluene or benzene), dialkyl amides (e.g. dimethyl formamide) cyclic ethers (e.g. tetrahydrofurane or dioxane), aliphatic ethers (e.g. diethyl ether) or acetonitrile. The excess of a liquid acid amide of the general Formula V (e.g. formamide) may also act as reaction medium.

According to method b, a compound of the Formula III is reacted with an acid of the Formula VIII. It is preferred to use an acid of the Formula VIII which contains the desired $A^-$ anion. The acid of the Formula VIII is used in an equimolar amount or in a small excess. As reaction medium preferably such inert organic solvents may be used in which the acid of the Formula VIII is sufficiently soluble. It is preferred to work in a lower alkanol (e.g. methanol or ethanol). The reaction takes place already at ambiant temperature but slight heating may be applied as well.

According to method c, compounds of the general Formula I, wherein $R_3$ is hydrogen, and $R_2$ stands for hydrogen, $C_{1-4}$ alkyl or unsubstituted phenyl, may be prepared by reacting a compound of the Formula IV with an ortho-ester of the Formula VI and treating the formimino ether of the Formula VII thus obtained with ammonia.

The ortho-ester of the Formula VI is selected depending on the definition of symbol $R_2$ in the desired compound of the general Formula I. Thus, if compounds of the general Formula I, wherein $R_2$ is hydrogen, are to be prepared, ortho-formic acid alkyl esters are used; it is preferred to apply a methyl or ethyl ester of the general Formula VI. The reaction of the compounds of the general Formulae IV and VI may be carried out in an inert solvent, e.g. a nitrile (such as acetonitrile) or an aromatic hydrocarbon (e.g. benzene or toluene). The excess of the starting material of the general Formula VI may also play the role of the reaction medium. The reaction may be accomplished under heating, advantageously at the boiling point of the reaction mixture.

The formimino ether of the general Formula VII thus obtained is reacted with ammonia, preferably with gaseous ammonia. The said reaction may be advantageously accomplished in an inert organic solvent, particularly in a lower alkanol (e.g. ethanol). The reaction takes place already at ambient temperature; one may generally work at 15-35 C.°. The ammonia may be preferably used in an equimolar amount or in a small excess of some %.

According to method d compounds of the general Formula I, wherein $R_3$ is $C_{1-4}$ alkyl, are prepared by reacting a compound of the general Formula II with a metal alcoholate containing 1-4 carbon atoms. It is preferred to use an alkali metal alcoholate (e.g. sodium or potassium alcoholate). As reaction medium any inert organic solvent may be used in which the alkali metal alcoholate is soluble. It is preferred to carry out the reaction in an alkanol corresponding to the alkali alcoholate used. Thus, if sodium methylate is used, methanol may be applied as reaction medium. The alkali metal alcoholate may be used in equimolar amount or in an excess of 10-100%. The reaction may be carried out preferably at 10-100 C.°.

According to method e compounds of the Formula I, wherein $R_3$ is hydrogen and $R_2$ stands for halogen, are prepared by reacting a compound of the Formula IV with urea in the presence of an organic solvent and a halogen-containing dehydrating agent. As halogen-containing dehydrating agent advantageously phosphorus oxychloride may be used. The reaction may be carried out in an inert organic solvent as medium; for this purpose advantageously solvents having a high boiling point (above 100 C.°) may be used.

The compound of the Formula I thus obtained may be separated into the isomers thereof by methods known per se, if desired.

In a compound of the Formula I thus obtained the $A^-$ anion may be exchanged for an other $A^-$ anion by methods known per se, if desired. Thus a compound of the Formula I, wherein $A^-$ is chloride, may be converted into the corresponding compound of the Formula I, wherein $A^-$ is perchlorate, by treatment with perchloric acid. Compounds of the Formula I, wherein $A^-$ is bromide, may be prepared from compounds of the Formula I, wherein $A^-$ is an other anion—e.g. a perchlorate anion—by reacting with tetrabutyl ammonium bromide.

A compound of the Formula I, wherein $A^-$ is ethane sulfonate, may be prepared by reacting a compound of the Formula I wherein $A^-$ is an other anion (e.g. bromide) with ethane sulfonic acid.

The starting materials of the Formula II, wherein $R_2$ is other than halogen, are known (DOS No. 3,128,386). The starting materials of the Formula II, wherein $R_2$ is halogen, can be prepared by methods analoguous to those described in the cited DOS.

The starting materials of the Formula III are in the Hungarian Patent application Ser. No. 3243/83. These compounds are prepared by reacting a compound of the Formula II with the aqueous solution of a base or with a $C_{1-4}$ metal alcoholate.

The starting materials of the Formula IV are disclosed in DOS No. 3,128,386.

The starting materials of the Formulae V and VI are readily available commercial products.

According to a further aspect of the present invention there are provided pharmaceutical compositions comprising as active ingredient at least one compound of the Formula I or an isomer thereof in admixture with suitable inert solid or liquid pharmaceutical carriers. The said pharmaceutical compositions may be prepared by methods of pharmaceutical industry known per se. The compositions may be finished in solid (e.g. tablets, pills, coated pills, dragees, capsules), semi-solid (e.g. ointments) or liquid (e.g. solutions, suspensions or emulsions) form. The compositions may be suitable for oral or parenteral administration.

The compositions of the present invention may contain carriers, e.g. solid carriers, fillers, sterile aqueous solutions or non-toxic organic solvents. The tablets suitable for oral administration may contain sweetening agents and/or other auxiliary agents (e.g. starch, particularly potato starch). The said compositions may also contain binding agents (e.g. polyvinyl pyrrolidone), sliding agents (e.g. magnesium stearate, sodium lauryl sulfate or talc), or other additives (e.g. sodium citrate, calcium carbonate, dicalcium phosphate etc.). The aqueous suspensions or elixirs suitable for oral administration may also comprise flavourants, dyestuffs, emulsifiers or diluents (e.g. water, ethanol, propylene glycol or glycerol etc.).

The pharmaceutical compositions for parenteral administration may comprise pharmaceutically acceptable solvents (e.g. sesame oil, peanut oil, aqueous propylene glycol, dimethyl formamide, etc.) or—when water-soluble active ingredients are used—water. The aqueous solutions may be adjusted to the desired pH-value by means of a buffer or to the isotonic values by using suitable liquid diluents (e.g. sodium chloride or glucose). The aqueous solutions are suitable first of all for intravenous, intramuscular or intraperitoneal administration. The sterile aqueous solutions may be prepared by methods known per se.

The daily dosage of the compounds of the general Formula I may vary between wide ranges and depends on various factors (e.g. the efficiency of the active ingredient, the method of administration, the state and condition of the patient etc.).

The pharmacological activity of the compounds of the general Formula I is shown by the following tests.

(1) ACUTE TOXICITY ON MICE

The test is carried out on male and female white mice belonging to the CFLP strain and weighing 18-22 g. The test compound is administered orally and the animals are observed for a period of 7 days. In the groups for each dose half of the animals are male and the other half are female. The animals are kept in a plastic box ($39 \times 12 \times 12$ cm) on scrapings litter at room temperature. The mice receive standard fodder and tap water ad libitum. The toxicity data are determined by the method of Litchfield-Wilcoxon.

The test compound is administered in an aqueous solution.

The results are summarized in Table I.

TABLE I

| Test compound | Toxicity on mice $LD_{50}$ mg/kg p.o. |
|---|---|
| Compound A | 410 |
| Compound B | 560 |
| Compound C | 590 |
| Reference compound D | 600 |
| Amitriptylin | 225 |

(2) ACUTE TOXICITY ON RATS

The test described in Paragraph 1 is carried out except that the observation period is 14 days and the animals are kept in boxes measuring $30 \times 39 \times 12$ cm; 5 animals per box.

The results are summarized in Table II.

TABLE II

| Test compound | Toxicity on rats $LD_{50}$ mg/kg p.o. |
|---|---|
| Compound A | 1300 |
| Compound B | about 1100 |
| Compound C | about 1030 |

(3) ANTAGONISM OF TETRABENAZINE PTOSIS, ON MICE AND RATS, P.O.

Groups of 10 mice each are treated orally with the test compound whereupon after 30 minutes 50 mg/kg of Tetrabenazine are administered intraperitoneally and the animals showing ptosis (eyelid-closure) are counted in each group after 30, 60, 90 and 120 minutes, respectively.

The results are evaluated as follows: on the basis of all the measured data an average ptosis is calculated for each group and the deviation from the average of the control group is expressed in percent (inhibition). The $ED_{50}$ values are calculated from the data thus obtained.

The results are summarized in Table III.

TABLE III

| | Antagonism of tetrabenazine ptosis on mice and rats | | | |
|---|---|---|---|---|
| | Mice | | Rats | |
| Test compound | $ED_{50}$ mg./kg. | Ther. index | $ED_{50}$ mg./kg. | Ther. index |
| Compound A | 0.3 | 1367 | 0.3 | 4333 |
| Compound B | 0.3 | 1867 | 1.0 | 1100 |
| Compound C | 2.9 | 203 | 5.4 | 191 |
| Reference compound D | 3.2 | 188 | 5.6 | 179 |

TABLE III-continued

Antagonism of tetrabenazine ptosis on mice and rats

| Test compound | Mice ED$_{50}$ mg./kg. | Ther. index | Rats ED$_{50}$ mg./kg. | Ther. index |
| --- | --- | --- | --- | --- |
| Amitriptyline | 12.0 | 19 | 11.5 | 46 |

(4) ANTAGONISM OF RESERPINE PTOSIS ON RATS, P.O.

Animal groups consisting of 10 rats each are treated subcutaneously with 2.5 mg./kg. of reserpine whereupon after 60 minutes the test compound is administered orally. The animals showing ptosis are counted until the effect decreases. The evaluation is carried out as described in connection with the previous ptosis test (test 3).

The results are summarized in the following Table IV.

TABLE IV

Antagonism of reserpine ptosis on rats

| Test compound | Rats ED$_{50}$ mg./kg. | Ther. index |
| --- | --- | --- |
| Compound A | 14 | 92.8 |
| Compound B | 28 | 39.3 |
| Compound C | 21 | 49.0 |
| Reference compound D | about 60 | 16.7 |
| Amitriptyline | about 140 | 3.6 |

(5) ANTIARRHYTHMIAL EFFECT ON RATS

The test is carried out according to the modified method of Marmo et al. The test animals are narcotized with ethyl urethane (1.2 g./kg. i.p.). Aconitine is administered intravenously in the form of a bolus injection in a dose of 75 µg./kg. The changes of ECG are followed in standard II outlet 5 minutes after the administration of aconitine. The changes observed are evaluated with the aid of a scale from 0 to 5 points. The test compound is administered either intravenously 2 minutes before the addition of aconitine, or orally 1 hour before the aconitine administration.

The results are summarized in Table V.

TABLE V

Antiarrhythmial effect on rats

| Test compound | ED$_{50}$ mg./kg. i.v. | p.o. | Ther. index |
| --- | --- | --- | --- |
| Compound A | 0.9 | 40 | 32.5 |
| Compound B | 1.6 | 30 | 27.5 |
| Lidocain | 4.0 (23.4%) | 120 (3.5%) | no ther. index can be calculated from these data; inactive |

(6) EFFECT ON BLOOD PRESSURE

When administered intravenously to narcotized cats the test compounds induce a uniform, long-lasting blood-pressure increase of 20–30 Hgmm.

(7) FURTHER EFFECTS

In addition to the above effects, the spasmolytic, local anaesthetic, analgesic, antiinflammatory and tranquillant-sedative activities are observed. Some compounds of the general Formula I exhibit tremorine antagonistic effect as well.

ANTIINFLAMMATORY EFFECT ON RATS

Into the planar surface of the hind leg of rats weighing 150–180 g. 0.1 ml. of 1% carrageenin is injected. The volume of the paw is determined before and 3 hours after the administration of the irritating agent with a plethysmometer. The animals are pre-treated with the test compound and the carrier (control), respectively, for an hour. Because of the different solubility properties Tween 80 as auxiliary agent is used.

The results are summarized in Table VI.

TABLE VI

Antiinflammatory effect on rats

| Test compound | Oedema inhibitory effect ED$_{50}$ mg./kg. | Ther. index |
| --- | --- | --- |
| Compound A | 24.5 | 53.1 |
| Reference compound D | can not be determined, no effect | — |
| Phenylbutazon | about 90.0 | 5.3 |

ANTITREMORINE EFFECT ON MICE 20 mg./kg. of tremorine are administered i.p. to mice whereupon after 45 minutes the induced characteristic tremor is registered. The test compounds are administered orally 1 hour before the addition of tremorine. The results are summarized in Table VII.

TABLE VII

Antitremorine effect on mice

| Test compound | Antitremorine effect ED$_{50}$ mg./kg. | Ther. index |
| --- | --- | --- |
| Compound B | 6 | 93.3 |
| Reference compound D | inactive | — |

The following test compounds are used:

Compound A = 1-(4-chloro-phenyl)-1-hydroxy-1,2-dihydro-as-triazino[6,1-a]isoquinolinium-ethanesulfonate (Example 2)

Compound B = 1-(4-chloro-phenyl)-1-hydroxy-1,2-dihydro-as-triazino[6,1-a]isoquinolinium-chloride (Example 4)

Compound C = 1-(4-chloro-phenyl)-1-hydroxy-1,2-dihydro-as-triazino[6,1-a]isoquinolinium-bromide (Example 1)

Reference compound D = 1-(4-chloro-phenyl)-as-triazino[6,1-a]isochinolinium-bromide (Example 5 of DOS No. 3,128,386)

Amitriptyline = N,N-dimethyl-3-[dibenzo[a,d]-cycloheptadiene-5-ylidene]-propylamine Lidocain = α-diethylamino-2,6-dimethyl-acetanilide Phenylbutazon = 4-butyl-1,2-diphenyl-3,5-pyrazolidine-dione Summarized it can be stated that the new compounds of the present invention possess outstanding antidepressant and antiarrhythmial effects. The activity of the compounds of the Formula I is by orders of magnitude higher than that of the most active compound disclosed in DOS No. 3,128,386 both in respect of the absolute dose and the therapeutical index on the tetrabenazine antagonism test on mice and rats.

On the reserpine ptosis test the activity of the new compounds of the present invention is 2–6 times higher than that of reference compound D. In addition to this surprising and unforeseen increase of effect, the activity spectrum of the compounds of the Formula I differs also qualitatively from that of the compounds disclosed in DOS No. 3,128,386 which manifests itself in the appearance of therapeutically highly favourable tranquillant, analgesic, spasmolytic, antiinflammatory and antitremorine effects.

The daily dosage of the compounds of the Formula I may vary between wide ranges and depends on various factors of the given case, as already mentioned above. As a matter of information it may be noted that the average oral daily dosage of the compounds of the Formula I is about 5–150 mg. which may be augmented up to 300 mg. in serious cases. The daily parenteral dose may amount approximately to 5–50 mg.

Further details of the present invention are to be found in the following Examples without limiting the scope of protection to the said Examples.

EXAMPLE 1

Preparation of 1-(4-chloro-phenyl)-1-hydroxy-1,2-dihydro-as-triazino[6,1-a]isoquinolinium-bromide A mixture of 2.0 g (0.0054 mole) of 1-(4-chloro-phenyl)-as-triazino[6,1-a]isoquinolinium-bromide, 10 ml of acetonitrile and 5 ml of water is stirred at room temperature. The starting material is temporarily dissolved, but later colourless crystals precipitate. Thus 1.5 g of the desired compound are obtained, yield, 71%, mp.: 270–271 C.°.

EXAMPLE 2

Preparation of 1-(4-chloro-phenyl)-1-hydroxy-1,2-dihydro-as-triazino[6,1-a]isoquinolinium-ethanesulfonate 3.55 g (0.0091 mole) of 1-(4-chloro-phenyl)-1-hydroxy-1,2-dihydro-as-triazino[6,1-a]isoquinolinium-bromide are reacted with 2.22 g (0.0022 mole) of ethane sulfonic acid in 50 ml of acetonitrile. The reaction mixture is evaporated to dryness and the residue dissolved in ethyl acetate. On cooling 3.3 g of the aimed compound precipitate in the form of prismatic crystals. Yield 86%. Mp.: 187–188 C.°.

EXAMPLE 3

Preparation of 1-(4-chloro-phenyl)-1-hydroxy-1,2-dihydro-as-triazino[6,1-a]isoquinolinium-perchlorate 3.5 g (0.008 mole) of 1-(4-chloro-benzoyl)-2-[N-(ethoxyimino-formyl)]isoquinolinium-perchlorate are treated with ammonia in 30 ml of ethanol whereupon the solvent is removed. The crystalline residue is dissolved in ethanol containing 5% of water and the solution is admixed with 5 ml of 70% perchloric acid. The product is extracted with nitro methane and the solvent is removed. Thus 1.64 g of the desired compound are obtained, yield 50%, mp.: 239–240 C.°.

The starting material can be prepared as follows:

A mixture of 4.55 g (0.010 mole) of 2-amino-1-(4-chloro-benzoyl)isoquinolinium-tosylate, 4.45 g (0.030 mole) of ethyl-ortho-formiate and acetonitrile is heated to boiling for an hour. The reaction mixture is cooled and the product precipitated by the addition of ether. Thus 4.4 g of 1-(4-chloro-benzoyl)-2-[N-(ethoxyiminoformyl)]isoquinolinium-tosylate are obtained. Yield 86%. Mp.: 183–184 C.°.

2.6 g (0.05 mole) of the above product are dissolved in 30 ml of thionyl chloride, the solution is heated to boiling for a short time and the excess of thionyl chloride is distilled off. The residue is treated with ether. Thus 1.7 g of yellow 1-(4-chloro-benzoyl)-2-[N-(ethoxyimino-formyl)]isoquinolinium-chloride are obtained, yield 90%, mp.: 158–160 C.°. After crystallization from acetonitrile 1.4 g of faint yellow needle crystals are obtained, yield 74%, mp.: 167–169 C.°.

3 g (0.006 mole) of the above product are dissolved in ethanol and 5 ml of 70% perchloric acid are added. The precipitated crystals are filtered off. Thus 2.3 g of crystalline 1-(4-chloro-benzoyl)-2-[N-(ethoxyimino-formyl)]isoquinolinium-perchlorate are obtained. Yield 90%, mp.: 224–225 C.° (from a mixture of acetonitrile and ether).

EXAMPLE 4

Preparation of 1-(4-chloro-phenyl)-1-hydroxy-1,2-dihydro-as-triazino[6,1-a]isoquinolinium-chloride To a solution of 3.1 g (0.01 mole) of 1-(4-chloro-phenyl)-1-hydroxy-1,2-dihydro-as-triazino[6,1-a]isoquinoline-5-ium-2-(1H)-ide and 15 ml of ethanol at room temperature 11 ml of hydrochloric acid /(1 mole/l) are added. After half an hour the product is precipitated by the addition of water. Thus 3 g of the desired compound are obtained, yield 87%, mp.: 227–228 C.°.

EXAMPLE 5

Preparation of 1-phenyl-1-hydroxy-1,2-dihydro-as-triazino[6,1-a]isoquinolinium-perchlorate A mixture of 10 g (0.024 mole) of 2-amino-1-benzoyl-isoquinolinium-tosylate, 30 ml of formamide and 15 ml of phosphorous oxychloride is heated at 80°–90 C.°. The reaction mixture is cooled, diluted with water and 10 ml of 70% perchloric acid are added. Thus 4.8 g of the aimed compound are obtained, yield 55%. Mp.: 245–246 C.° (after crystallization from a mixture of acetonitrile and water).

EXAMPLE 6

Preparation of 1-(4-chloro-phenyl)-1-hydroxy-1,2-dihydro-as-triazino[6,1-a]isoquinolinium-perchlorate A mixture of 5 g (0.013 mole) of 2-amino-1-(p-chloro-benzoyl)-isoquinolinium-perchlorate, 8 ml of titanium tetrachloride and 40 ml of formamide is heated at 90–100 C.° for an hour whereupon 10 ml of water are added. When the precipitation of crystals has begun, a solution of 5 g of sodium perchlorate and 10 ml of water is added. Thus 3.0 g of the aimed compound are obtained, yield 56%, mp.: 238–239 C.° (from a mixture of acetonitrile and water).

EXAMPLE 7

Preparation of 1-(4-chloro-phenyl)-1-methoxy-1,2-dihydro-as-triazino[6,1-a]isoquinolinium-chloride One proceeds according to Example 4 except that 3.23 g (0.01 mole) of 1-(4-chloro-phenyl)-1-methoxy-as-triazino[6,1-a]isoquinolin-5-ium-2-(1H)-ide is used. Yield 85%, mp.: 158–160 C.°.

EXAMPLE 8

Preparation of 4-(4-chloro-phenyl)-4-hydroxy-3,4-dihydro-as-triazino[1,6-a]quinolinium-perchlorate A mixture of 5 g (0.011 mole) of 1-amino-2-(4-chloro-benzoyl)-quinolinium-tosylate, 30 ml of formamide and 20 ml of phosphorous oxychloride is heated at 90 C.° for an hour. The reaction mixture is poured onto water and after an hour 70% perchloric acid is added. Thus 3.3 g of the aimed compound are obtained, yield 73%, mp.: 293–294 C.° (from a mixture of nitro methane and ether).

EXAMPLE 9

Preparation of 1-(4-chloro-phenyl)-1-hydroxy-1,2-dihydro-pyrido[2,1-f]-as-triazinium-perchlorate One proceeds according to Example 6 except that 11 g (0.027 mole) of 1-amino-2-(4-chloro-benzoyl)-pyridinium-tosylate are used as starting material. Yield 79.5%, mp.: 254–255 C.° (from acetonitrile).

EXAMPLE 10

Preparation of 1-phenyl-1,3-dihydroxy-1,2-dihydro-pyrido[2,1-f]-as-triazinium-perchlorate 2.6 g (0.0087 mole) of 1-amino-2-benzoyl-pyridinium-perchlorate are reacted with 5.2 g (0.0087 mole) of urea in polyphosphoric acid at 160 C.°. The reaction mixture is poured into water and the mixture is saturated with sodium perchlorate. Thus 1.8 g of the aimed compound are obtained, yield 64%, mp.: 263–264 C.°.

EXAMPLE 11

Preparation of 1-(4-chloro-phenyl)-1-hydroxy-1,2-dihydro-pyrido[2,1-f]-as-triazinium-bromide One proceeds according to Example 1 except that 1-(4-chloro-phenyl)-pyrido[2,1-f]-as-triazinium-bromide is used as starting material.

Yield 87%, mp.: 280–281 C.°.

EXAMPLE 12

Preparation of 1-(4-chloro-phenyl)-1-methoxy-1,2-dihydro-as-triazino[6,1-a]isoquinolinium-perchlorate To 3.91 g (0.01 mole) of 1-(4-chloro-phenyl)-as-triazino[6,1-a]isoquinolinium-perchlorate methanol containing 0.02 mole of sodium methylate is added. The aimed compound is precipitated by the addition of 8 ml of 7% aqueous perchloric acid. Yield 83%. Mp.: 158–159 C.°.

What we claim is:

1. A condensed as-triazinium derivative of the Formula I

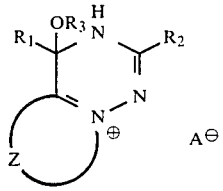

and isomers thereof wherein
$R_1$ stands for $C_{1-10}$ alkyl or phenyl or naphthyl, wherein the two latter groups may be optionally substituted by one or more halogen, nitro, amino, hydroxy, $C_{1-4}$ alkyl and/or $C_{1-4}$ alkoxy substituent(s);
$R_2$ is hydrogen, $C_{1-4}$ alkyl, hydroxy, halogen or phenyl or naphthyl, wherein the two latter groups may be optionally substituted by one or more halogen, nitro, amino, hydroxy, $C_{1-4}$ alkyl and/or $C_{1-4}$ alkoxy substituent(s);
$R_3$ represents hydrogen or $C_{1-4}$ alkyl;
Z is buta-1,3-dienyl or a group of the Formula (a)

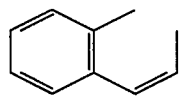

or (b)

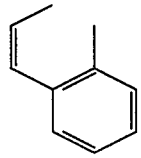

and
$A^-$ is an anion.

2. A compound according to claim 1, wherein Z is a group of the Formula (b).

3. A compound as in claim 2, wherein $R_1$ is 4-chlorophenyl.

4. A compound according to claim 1, wherein $R_1$ is phenyl optionally substituted by one or more halogen atoms.

5. 1-(4-Chloro-phenyl)-1-hydroxy-1,2-dihydro-as-triazino[6,1-a]isoquinolinium-ethanesulfonate.

6. 1-(4-Chloro-phenyl)-1-hydroxy-1,2-dihydro-as-triazino[6,1-a]isoquinolinium-chloride.

7. Antidepressant and antiarrhythmial composition which comprises: an effective antidepressant and antiarrhythmial amount of a compound of the formula I as defined in claim 1 or an isomer thereof in admixture with a pharmaceutically acceptable carrier and/or excipient.

8. An antidepressant and antiarrhythmial composition as defined in claim 7, wherein the active compound is 1-(4-chloro-phenyl)-1-hydroxy-1,2-dihydro-as-triazino[6,1-a]isoquinolinum-ethanesulfonate.

* * * * *

UNITED STATES PATENT AND TRADEMARK OFFICE
CERTIFICATE OF CORRECTION

PATENT NO. :   4,602,018

DATED      :   July 22, 1986

INVENTOR(S) :  Andras MESSMER; Gyorgy HAJOS; Pal BENKO; Eva FURDYGA; Lujza PETOCZ It is certified that error appears in the above-identified patent and that said Letters Patent is hereby corrected as shown below:

[75] add: Last 5 inventors names

Éva FURDYGA; Lujza PETÓCZ; Katalin Grasser; Ibolya KOSÓCZKY; and Enikö SZIRT née KISZELLY Signed and Sealed this Eighteenth Day of November, 1986

Attest:

DONALD J. QUIGG

Attesting Officer      Commissioner of Patents and Trademarks